US012788423B2

(12) United States Patent
Moore et al.

(10) Patent No.: US 12,788,423 B2
(45) Date of Patent: Nov. 10, 2026

(54) IMPLANT REMOVAL DEVICES AND METHODS

(71) Applicants: Russell David Moore, Jersey City, NJ (US); Choon Hyong Lee, Irvine, CA (US)

(72) Inventors: Russell David Moore, Jersey City, NJ (US); Choon Hyong Lee, Irvine, CA (US)

(73) Assignee: Russell David Moore, Jersey City, NJ (US)

( * ) Notice: Subject to any disclaimer, the term of this patent is extended or adjusted under 35 U.S.C. 154(b) by 177 days.

(21) Appl. No.: 18/467,966

(22) Filed: Sep. 15, 2023

(65) Prior Publication Data

US 2024/0115283 A1 Apr. 11, 2024

Related U.S. Application Data

(60) Provisional application No. 63/413,295, filed on Oct. 5, 2022.

(51) Int. Cl.
*A61B 17/30* (2006.01)

(52) U.S. Cl.
CPC ........ *A61B 17/30* (2013.01); *A61B 2017/301* (2013.01)

(58) Field of Classification Search
CPC .................... A61B 17/50; A61B 17/30; A61B 2017/301–305; A61B 2017/505; A61B 17/3468; A61B 17/28–295; A61P 15/18; A61F 6/06; A61F 6/12
USPC .................................................. 606/151, 210
See application file for complete search history.

(56) References Cited

U.S. PATENT DOCUMENTS

| | | | | |
|---|---|---|---|---|
| 4,442,837 A * | 4/1984 | Keatley | A61D 1/00 606/1 |
| 6,283,984 B1 * | 9/2001 | Ray | A61B 17/30 606/205 |
| 6,517,554 B1 * | 2/2003 | Zhu | A61B 17/30 606/205 |
| 9,844,377 B2 * | 12/2017 | Peterson | A61B 17/10 |
| 10,653,405 B2 | 5/2020 | Kass et al. | |
| 10,722,259 B2 | 7/2020 | Bratlie et al. | |
| 10,925,639 B2 | 2/2021 | Smith et al. | |

(Continued)

OTHER PUBLICATIONS

International Searching Authority, "International Search Report and the Written Opinion", Application No. PCT/US2023/074304, Mailed Feb. 5, 2024, pp. 1-13.

*Primary Examiner* — Elizabeth Houston
*Assistant Examiner* — Serenity A Miller
(74) *Attorney, Agent, or Firm* — Fredrikson & Byron, P.A.

(57) ABSTRACT

An implant removal device includes a body, a first arm, a second arm, an actuation interface, and an extraction member. The first arm is supported at the body and configured to move relative to the body between a retracted position and a skin gripping position. The second arm is supported at the body and configured to move relative to the body between the retracted position and the skin gripping position. The actuation interface is supported at the body. The actuation interface is configured to receive a first actuation input thereat to cause at least one of the first arm and the second arm to move from the skin gripping position to the retracted position. The extraction member is supported at the body and located between the first arm and the second arm.

14 Claims, 11 Drawing Sheets

(56) References Cited

U.S. PATENT DOCUMENTS

| | | | | |
|---|---|---|---|---|
| 2006/0074435 | A1* | 4/2006 | Seil | A61F 2/1664 606/107 |
| 2011/0221217 | A1* | 9/2011 | Grosse | B25B 9/02 294/99.2 |
| 2018/0168673 | A1* | 6/2018 | Bratlie | A61B 17/50 |
| 2020/0078035 | A1* | 3/2020 | Britland | B33Y 80/00 |
| 2021/0322056 | A1 | 10/2021 | Moore et al. | |
| 2021/0393283 | A1* | 12/2021 | Goerlitz-Jessen | A61F 2/1664 |
| 2023/0132741 | A1* | 5/2023 | Fleming | A61B 17/3468 606/167 |

* cited by examiner

IMPLANT REMOVAL DEVICES AND METHODS

RELATED CASES

This application claims priority to U.S. provisional patent application No. 63/413,295, filed on Oct. 5, 2022, the contents of which are hereby incorporated by reference.

TECHNICAL FIELD

This disclosure relates generally to implant removal devices and related methods of using an implant removal device to remove an implant. In particular, embodiments are described herein in the context of subdermal implant removal devices and methods.

BACKGROUND

Implants are used for a variety of medical purposes at various anatomical locations. For instance, certain types of implants are positioned underneath the skin and referred to as subdermal implants. One common type of subdermal implant is a long-term contraceptive. This long-term contraceptive is generally in the form of a rod and implanted underneath the skin of a patient where it releases one or more contraceptive hormones, such as a synthetic progestin etonogestrel, for a period of time. Because the contraceptive subdermal implant is non-biodegradable, it must be removed once the one or more contraceptive hormones it carries are depleted. In general, contraceptive subdermal implants are removed and replaced every two to three years, depending on the particular type of contraceptive implant.

However, current techniques for removing subdermal implants, including generally rod form contraceptive subdermal implants, are time-consuming and tedious for the clinician and uncomfortable, oftentimes even painful, for the patient. Subdermal implants are generally removed in an ad hoc, manual manner without a standardized removal technique. In general, these current techniques involve the clinician using one hand to variably manipulate the skin around the subdermal implant while using the other hand to attempt to align the subdermal implant with a previously formed incision at the skin and force the subdermal implant out from underneath the skin through the incision. As such, this process entails a significant amount of trial and error. Given the imprecise nature of the current manual, ad hoc technique for removing a subdermal implant, it oftentimes can take several cycles of this hands-on process to ultimately remove the implant from underneath the patient's skin.

SUMMARY

In general, various embodiments relating to implant removal devices and related methods are disclosed herein. In particular, the implant removal device and method embodiments disclosed herein can be particularly useful as subdermal implant removal devices and methods. These embodiments can facilitate efficient removal of a subdermal implant in a manner that can reduce clinician time and effort and decrease patient discomfort. Moreover, these embodiments can provide this efficient subdermal implant removal solution in a manner that is repeatable across varying anatomical characteristics from patient-to-patient and, thus, provide a more standardized subdermal implant removal solution. These embodiments can accomplish such advantages by optimizing the application of force at the skin surface adjacent the subdermal implant and thereby optimize resulting changes to surface tension at the skin surface adjacent the subdermal implant to thereby alter the positioning of the subdermal implant in a manner that can increase the precision of implant removal through an incision at the skin.

One embodiment includes an implant removal device. This implant removal device embodiment includes a body, a first arm, a second arm, an actuation interface, and an extraction member. The first arm is supported at the body and configured to move relative to the body between a retracted position and a skin gripping position. The second arm is supported at the body and configured to move relative to the body between the retracted position and the skin gripping position. The actuation interface is supported at the body. The actuation interface is configured to receive an actuation input thereat to cause at least one (e.g., both) of the first arm and the second arm to move from the retracted position to the skin gripping position. The extraction member is supported at the body and located between the first arm and the second arm.

In a further embodiment of this implant removal device, the extraction member is configured to contact a skin surface adjacent a first end of an implant. When moved, relative to the body, to the skin gripping position (e.g., as a result of application of the actuation input), the first and second arms are configured to contact and raise respective skin surfaces on opposite sides of the implant (e.g., respective skin surfaces on opposite longitudinal sides of the implant each extending between the first end and an opposite second end of the implant). With the first and second arms in the skin gripping position, the extraction member can be configured to move (e.g., moved with the body) toward an incision at the skin surface (e.g., toward an incision at a location at the skin surface adjacent a second end of the implant that is opposite the first end of the implant). As the extraction member is moved, the extraction member is configured to urge the implant toward the incision at the skin surface while the first and second arms are in the skin gripping position. As the extraction member is so moved, the first and second arms can be maintained in the skin gripping position (e.g., as a result of maintaining the actuation input at the actuation interface while the extraction member is moved).

In a further embodiment of this implant removal device, as the first arm is moved from the retracted position to the skin gripping position, the first arm can be configured to contact and raise a skin surface at a first side (e.g., first longitudinal side) of the implant. And, as the second arm is moved from the retracted position to the skin gripping position, the second arm can be configured to contact and raise the skin surface at a second side (e.g., second longitudinal side) of the implant. This second side can be opposite the first side. In some examples, the extraction member can be located between the first arm and the second arm when the first arm and the second arm are in the skin gripping position. And, the extraction member can be configured to engage a skin surface adjacent a first end portion of the implant, which extends between the first side of the implant and the second side of the implant, when the first arm and the second arm are in the skin gripping position.

In a further embodiment of this implant removal device, the actuation interface includes a first actuation interface at the first arm and a second actuation interface at the second arm. The first actuation interface is configured to receive a first actuation input thereat to cause the first arm to move from the retracted position to the skin gripping position. The first arm can be configured to be maintained in the skin gripping position while the first actuation input is maintained at the first actuation interface, and the first arm can be configured to move from the skin gripping position to the retracted position when the first actuation input is removed. For instance, the first arm can be biased (e.g., via a biasing force applied at the first arm by the body of the implant removal device) to the retraced position and that bias can be overcome by application of the first actuation input to move the first arm from the biased, retracted position to the skin gripping position. The second actuation interface is configured to receive a second actuation input thereat to cause the second arm to move from the retracted position to the skin gripping position. The second arm can be configured to be maintained in the skin gripping position while the second actuation input is maintained at the second actuation interface, and the second arm can be configured to move from the skin gripping position to the retracted position when the second actuation input is removed. For instance, the second arm can be biased (e.g., via a biasing force applied at the second arm by the body of the implant removal device) to the retraced position and that bias can be overcome by application of the second actuation input to move the second arm from the biased, retracted position to the skin gripping position. Such configurations of the first and second arms can be useful in allowing for more precise control over the application of force at the skin surface via the first and second arms. For example, a user can apply the first actuation input at the first actuation interface at the first arm via one portion (e.g., one finger) of one hand of the user and the user can apply the second actuation input at the second actuation interface at the second arm via another portion (e.g., another finger) of the one hand of the user. This can facilitate more precise control over the degree of force imparted at each of the skin surfaces in contact with, and adjacent, the first and second arms by allowing for a user to incrementally modulate the extent to which the first and second arms are moved to the skin gripping position as suited for a specific application at a particular patient. And, this can facilitate the ability to apply different degrees of force at the first and second arms (e.g., via different degrees of the first and second actuation inputs applied via the different fingers of the user) and thus the ability to move the first and second arms to different extents as need when moving from the retracted position to such differential first and second arm skin gripping positions. This can be useful in facilitating efficient and precise implant removal across various anatomic characteristics from patient-to-patient.

In a further embodiment of this implant removal device, a space defined between the first arm and the second arm is greater when the first arm and the second arm are in the retracted position than when the first arm and the second arm are in the skin gripping position. Also, each of the first arm and the second arm can be biased to the retracted position. In some such examples, the body can be configured to impart a biasing force on each of the first arm and the second arm to bias each of the first arm and the second arm to the retracted position. The body can be configured such that the biasing force is overcome by application of the actuation input at the actuation interface to cause each of the first arm and the second arm to move from the retracted position to the skin gripping position. And, the body can be configured such that, upon removal of the actuation input at the actuation interface, the biasing force moves each of the first arm and the second arm from the skin gripping position to the retracted position.

In a further embodiment of this implant removal device, the actuation interface can include the first actuation interface at the first arm and the second actuation interface at the second arm. The first actuation interface can include a first flange, at the first arm, extending out from the first arm, and the second actuation interface can include a second flange, at the second arm, extending out from the second arm. The first flange can be configured to receive the first actuation input thereat to cause the first arm to move from the retracted position to the skin gripping position, and the second flange can be configured to receive the second actuation input thereat to cause the second arm to move from the retracted position to the skin gripping position. The body can include a biasing member that is configured to impart a biasing force on each of the first arm and the second arm to bias each of the first arm and the second arm to the retracted position. The first flange can be supported at the first arm at a first side of the biasing member, and the second flange can be supported at the second arm at a second side of the biasing member, where the second side is opposite the first side. As one particular example, the biasing member can include a C-shaped element having a first C-shaped end and a second C-shaped end opposite the first C-shaped end. And, the first flange can be supported at the first arm adjacent the first C-shaped end, and the second flange can be supported at the second arm adjacent the second C-shaped end.

In a further embodiment of this implant removal device, the first arm includes a first skin interfacing surface and the second arm includes a second skin interfacing surface. The first skin interfacing surface includes a first implant support member at a lower portion of the first arm, and the second skin interfacing surface includes a second implant support member at a lower portion of the second arm. The first implant support member can extend out from the first skin interfacing surface at the first arm in a direction toward the second arm, and the second implant support member can extend out from the second skin interfacing surface at the second arm in a direction toward the first arm.

For example, the implant removal device embodiments described immediately above can be configured to reduce the likelihood of implant breakage during removal by supporting the implant along its longitudinal axis. Current techniques for removing a subdermal implant, such as that described in the Background, can cause the implant to break before it is removed from underneath the skin surface. This can result because these current techniques apply relatively high localized pressure at a small number of, or single, discrete portion(s) of the implant. In the case of an elongated rod subdermal implant, these current techniques may apply relatively high localized pressure at a smaller region along the implant's longitudinal axis (e.g., via a clinician's fingers pinching the rod on both sides). Embodiments of the implant removal device embodiment disclosed herein can reduce the likelihood that the implant breaks during removal by better distributing forces along the implant's longitudinal axis. For example, the implant removal device can include the first and second arms each configured to apply a force at the skin surface along at least a portion of a length of the implant as measured along its longitudinal axis. In this way, the first and second arms of the implant removal device can support the implant along its longitudinal axis at locations adjacent along each lateral side of the implant and thereby can reduce the likelihood that the implant breaks during the removal process.

Another embodiment includes a method of removing a subdermal implant that is located beneath the skin surface. This method embodiment includes positioning an implant removal device at a skin surface. When the implant removal device is positioned at the skin surface, the implant removal device (e.g., via an extraction member of the implant removal device) can be configured to contact the skin surface adjacent a first end of the subdermal implant and cause a second, opposite end surface of the subdermal implant to move and be angled generally upward toward the skin surface. Once the implant removal device is positioned at the skin surface, one or more arms of the implant removal device are moved to a skin gripping position. When the one or more arms are moved to the skin gripping position, the one or more arms can be configured to contact and raise respective skin surfaces on opposite longitudinal sides of the subdermal implant. The method also includes making an incision at the skin surface, for instance, when the implant removal device is positioned at the skin surface (e.g., such that the extraction member is in contact with the skin surface adjacent the first end of the subdermal implant) and the one of more arms are in the skin gripping position. The method can further include moving an extraction member of the implant removal device (e.g., moving the extraction member with a body of the implant removal device) along the skin surface in a direction toward the incision. And, the method can further include removing the subdermal implant through the incision.

In a further embodiment of this method, positioning the implant removal device at the skin surface can include initially positioning the extraction member in contact with the skin surface adjacent the first end of the subdermal implant with each of the first arm and the second arm in the retracted position. Initially positioning the extraction member in contact with the skin surface adjacent the first end of the subdermal implant can cause a second, opposite end of the subdermal implant to move and be angled generally upward toward the skin surface. Then, with the extraction member positioned in contact with the skin surface adjacent the first end of the subdermal implant (e.g., and the second, opposite end of the subdermal implant has been caused to move and be angled generally upward toward the skin surface), this further embodiment of the method can include moving each of the first arm and the second arm to the skin gripping position (e.g., via application of the actuation input) such that the first arm is positioned adjacent a first longitudinal side of the subdermal implant and the second arm is positioned adjacent a second longitudinal side of the subdermal implant. The second longitudinal side is opposite the first longitudinal side, and the first arm and the second arm are closer together in the skin gripping position than in the retracted position.

In a further embodiment of this method, the incision can be created after the implant removal device is positioned at the skin surface and/or after the first and second arms have been moved to the skin gripping position and before moving the extraction member along the skin surface and removing the subdermal implant. For example, the incision can be created at the skin surface at a location opposite the extraction member and between the first and second arms that are in the skin gripping position.

In a further embodiment of this method, when moving the first arm from the retracted position to the skin gripping position, the skin surface can be contacted at the first longitudinal side of the subdermal implant with a first skin interfacing surface of the first arm, and that skin surface can be raised at the first longitudinal side of the subdermal implant. And, when moving the second arm from the retracted position to the skin gripping position, the skin surface can be contacted at the second longitudinal side of the subdermal implant with a second skin interfacing surface of the second arm, and that skin surface can be raised at the second longitudinal side of the subdermal implant. Raising the skin surface at the first longitudinal side of the subdermal implant and raising the skin surface at the second longitudinal side of the subdermal implant can include raising the subdermal implant.

Another embodiment includes an implant removal device. This implant removal device embodiment includes a body, a first arm supported at the body, a second arm supported at the body, an actuation interface supported at the body, and an extraction member supported at the body. The first arm is configured to move relative to the body between a first arm retracted position and a first arm skin gripping position. The second arm is configured to move relative to the body between a second arm retracted position and a second arm skin gripping position. The actuation interface is configured to receive an actuation input to cause at least one of: (i) the first arm to move between the first arm retracted position and the first arm skin gripping position, and (ii) the second arm to move between the second arm retracted position and the second arm skin gripping position. The extraction member is located between the first arm and the second arm.

In a further embodiment of this device, the body is configured to bias the first arm to the first arm retracted position and the second arm to the second arm retracted position, and the actuation interface is configured to receive the actuation input to cause both: (i) the first arm to move from the first arm retracted position to the first arm skin gripping position, and (ii) the second arm to move from the second arm retracted position to the second arm skin gripping position. For example, the actuation interface can include a first actuation interface at the first arm and a second actuation interface at the second arm. The first actuation interface can be configured to receive the actuation input to cause the first arm to move from the first arm retracted position to the first arm skin gripping position, and the second actuation interface can be configured to receive the actuation input to cause the second arm to move from the second arm retracted position to the second arm skin gripping position. In some such examples, the first arm can be configured to be maintained at the first arm skin gripping position while the actuation input is maintained at the first actuation interface and the first arm can be configured to move, as a result of the bias, from the first arm skin gripping position to the first arm retracted position when the actuation input is removed from the first actuation interface. Similarly, in some such examples, the second arm can be configured to be maintained at the second arm skin gripping position while the actuation input is maintained at the second actuation interface and the second arm can be configured to move, as a result of the bias, from the second arm skin gripping position to the second arm retracted position when the actuation input is removed from the second actuation interface. For instance, the first actuation interface can include a first flange that extends out from the first arm and is configured to receive the actuation input via at least a first finger of a first hand at the first flange, and the second actuation interface can include a second flange that extends out from the second arm and is configured to receive the actuation input via at least a second finger of the first hand at the second flange. The body can include a biasing member that is configured to impart a biasing force at each of the first arm and the second arm to bias the first arm to the first arm retracted position and the second arm to the second arm retracted position. In one particular such example, the biasing member can include a C-shaped element having a first element end and a second element end that is opposite the first element end, and the first flange can be supported at the first arm adjacent the first element end and the second flange can be supported at the second arm adjacent the second element end.

In a further embodiment of this device, the implant removal device can additionally include a first skin interfacing extension at a side of the first arm opposite the first actuation interface and a second skin interfacing extension at a side of the second arm opposite the second actuation interface. The first skin interfacing extension can extend out from the first arm toward the second arm, and the second skin interfacing extension can extend out from the second arm toward the first arm. For example, the first skin interfacing extension can be configured to serve as a contact point, at the first arm, with a skin surface at which the implant removal device is positioned so as to contact and raise up the skin surface adjacent the first arm. And the second skin interfacing extension can be configured to serve as a contact point, at the second arm, with the skin surface at which the implant removal device is positioned so as to contact and raise up the skin surface adjacent the second arm.

In a further embodiment of this device, when the implant removal device is positioned at a skin surface, the extraction member can be configured to contact the skin surface adjacent a first end of an implant that extends between a first longitudinal side of the implant and a second longitudinal side of the implant. Also when the implant removal device is positioned at the skin surface and the first arm is at the first arm skin gripping position, the first arm can be configured to contact the skin surface adjacent the first longitudinal side of the implant. And when the implant removal device is positioned at the skin surface and the second arm is at the second arm skin gripping position, the second arm can be configured to contact the skin surface adjacent the second longitudinal side of the implant. For example, the first arm can be configured, when moved from the first arm retracted position to the first arm skin gripping position, to contact and raise upward the skin surface adjacent the first longitudinal side of the implant, and the second arm can be configured, when moved from the second arm retracted position to the second arm skin gripping position, to contact and raise upward the skin surface adjacent the second longitudinal side of the implant. In addition, as the extraction member is moved toward an incision at the skin surface and with the first arm in the first arm skin gripping position and the second arm in the second arm skin gripping position, the extraction member can be configured to urge the implant toward the incision. For instance, the extraction member can be positioned below the first arm and the second arm and the extraction member defines a bottom-most surface of the implant removal device.

An additional embodiment include an implant removal device. This implant removal device embodiment includes a body, a first arm supported at the body, a second arm supported at the body, an actuation interface supported at the body, and an extraction member supported at the body. The first arm can be configured to move relative to the body between a first arm retracted position and a first arm skin gripping position. The second arm can be configured to move relative to the body between a second arm retracted position and a second arm skin gripping position. The actuation interface can be configured to receive an actuation input to cause at least one of: (i) the first arm to move between the first arm retracted position and the first arm skin gripping position, and (ii) the second arm to move between the second arm retracted position and the second arm skin gripping position. When the implant removal device is positioned at a skin surface, the extraction member can be configured to contact the skin surface between the first arm and the second arm and adjacent a first end of an implant that extends between a first longitudinal side of the implant and a second longitudinal side of the implant.

In a further embodiment of this device, when the implant removal device is positioned at the skin surface and the first arm is at the first arm skin gripping position, the first arm can configured to contact the skin surface adjacent the first longitudinal side of the implant, and, when the implant removal device is positioned at the skin surface and the second arm is at the second arm skin gripping position, the second arm can be configured to contact the skin surface adjacent the second longitudinal side of the implant. For example, the first arm can be configured, when moved from the first arm retracted position to the first arm skin gripping position, to contact and raise upward the skin surface adjacent the first longitudinal side of the implant, and the second arm can be configured, when moved from the second arm retracted position to the second arm skin gripping position, to contact and raise upward the skin surface adjacent the second longitudinal side of the implant. Additionally, in a further such example, as the extraction member is moved toward an incision at the skin surface and with the first arm in the first arm skin gripping position and the second arm in the second arm skin gripping position, the extraction member can be configured to urge the implant toward the incision.

In a further embodiment of this device, the body can be configured to bias the first arm to the first arm retracted position and the second arm to the second arm retracted position, and the actuation interface can be configured to receive the actuation input to cause both: (i) the first arm to move from the first arm retracted position to the first arm skin gripping position, and (ii) the second arm to move from the second arm retracted position to the second arm skin gripping position. For example, the actuation interface can include a first actuation interface at the first arm and a second actuation interface at the second arm. The first actuation interface can include a first flange that extends out from the first arm and is configured to receive the actuation input via at least a first finger of a first hand at the first flange to cause the first arm to move from the first arm retracted position to the first arm skin gripping position. The second actuation interface can include a second flange that extends out from the second arm and is configured to receive the actuation input via at least a second finger of the first hand at the second flange to cause the second arm to move from the second arm retracted position to the second arm skin gripping position. In an additional or alternative example, the first arm can be configured to be maintained at the first arm skin gripping position while the actuation input is maintained at the first actuation interface and the first arm can be configured to move, as a result of the bias, from the first arm skin gripping position to the first arm retracted position when the actuation input is removed from the first actuation interface. And the second arm can be configured to be maintained at the second arm skin gripping position while the actuation input is maintained at the second actuation interface and the second arm can be configured to move, as a result of the bias, from the second arm skin gripping position to the second arm retracted position when the actuation input is removed from the second actuation interface.

The details of one or more examples are set forth in the accompanying drawings and the description below. Other features, objects, and advantages will be apparent from the description and drawings.

BRIEF DESCRIPTION OF THE DRAWINGS

The following drawings are illustrative of particular embodiments of the present invention and, therefore, do not limit the scope of the invention. The drawings are intended for use in conjunction with the explanations in the following description. Embodiments of the invention will hereinafter be described in conjunction with the appended drawings, wherein like numerals denote like elements. The features illustrated in the drawings are not necessarily to scale, though embodiments within the scope of the present invention can include one or more of the illustrated features (e.g., each of the illustrated features) at the scale shown. For example, certain dimensional measurements may be shown in certain of the drawing figures and while embodiments within the scope of the present disclosure can include such features at the shown dimensional measurements, other embodiments within the scope of the present disclosure can include variations of different dimensional measurements for these same features.

DETAILED DESCRIPTION

The following detailed description is exemplary in nature and is not intended to limit the scope, applicability, or configuration of the invention in any way. Rather, the following description provides some practical illustrations for implementing embodiments of the present invention. Examples of constructions, materials, and/or dimensions are provided for selected elements though it is to be understood that other constructions, materials, and/or dimensions are within the scope of the present disclosure. Those skilled in the art will recognize that many of the noted examples have a variety of suitable alternatives.

Figure 1:
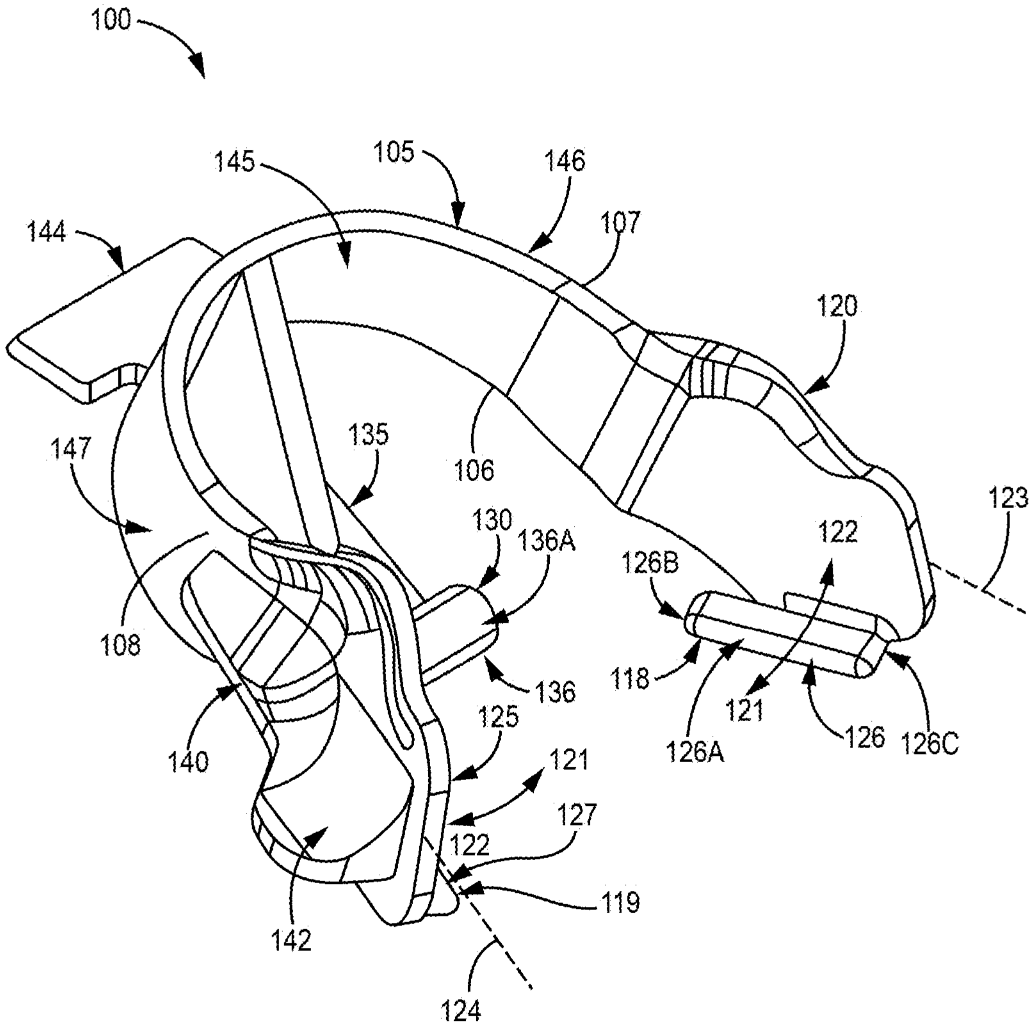
FIG. 1 is a perspective view of an embodiment of an implant removal device.
Figure 2:
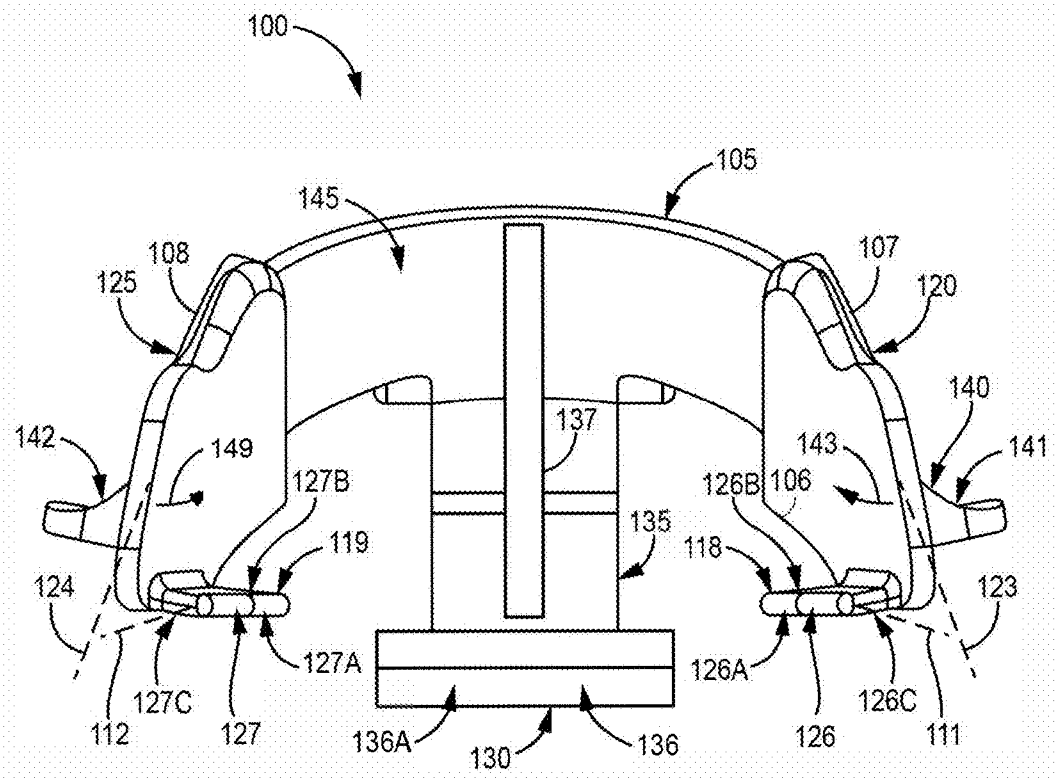
FIG. 2 is a front end elevational view of the implant removal device of FIG. 1.
Figure 3:
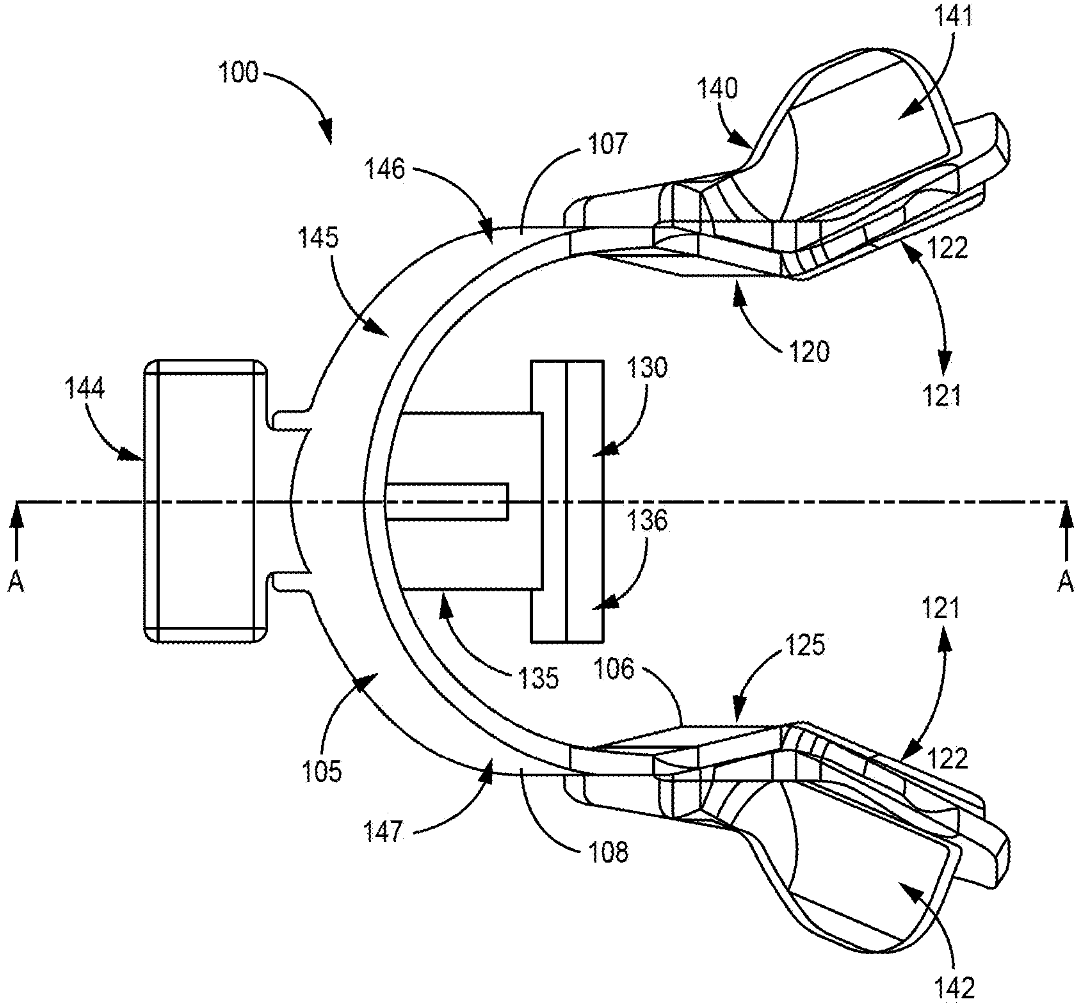
FIG. 3 is a top plan view of the implant removal device of FIG. 1.
Figure 4:
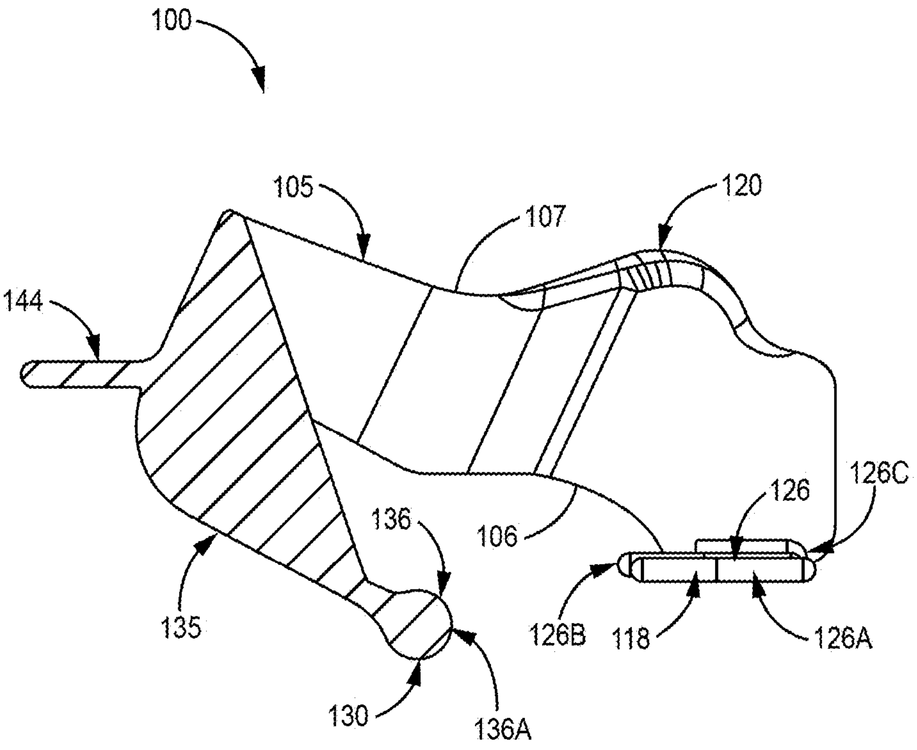
FIG. 4 is a longitudinal cross-sectional view of the implant removal device of FIG. 1, taken along longitudinal line A-A in FIG. 3.
Figure 5:
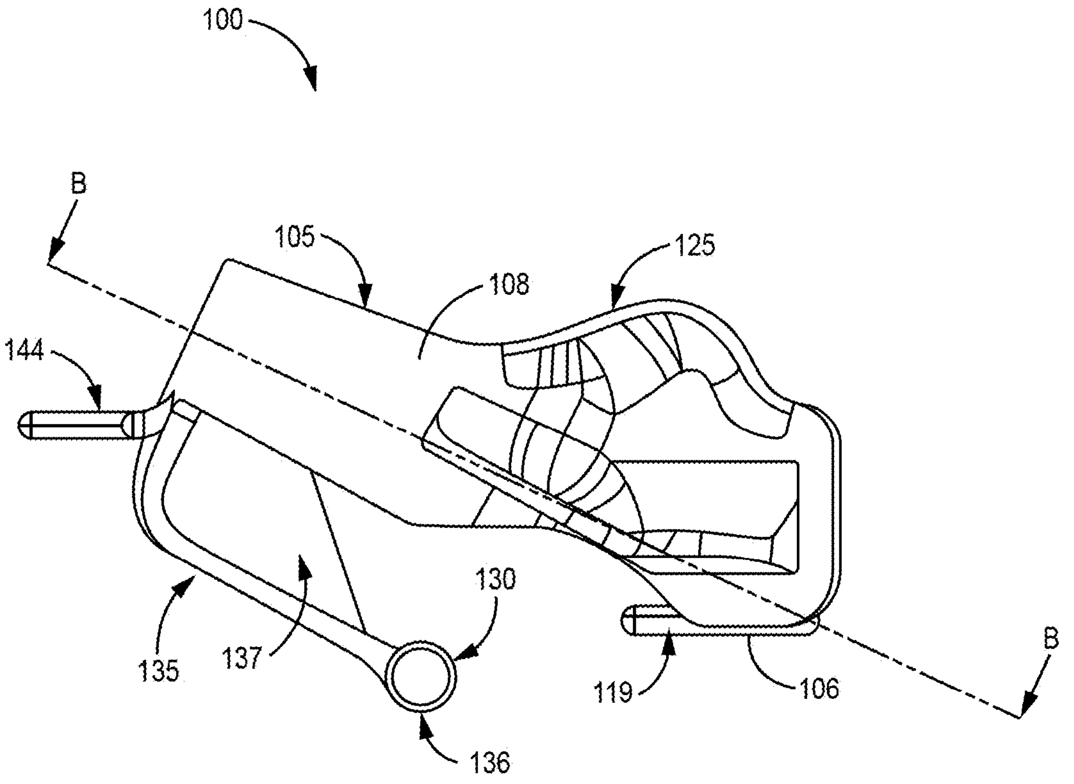
FIG. 5 is a longitudinal side elevational view of the implant removal device of FIG. 1.
Figure 6:
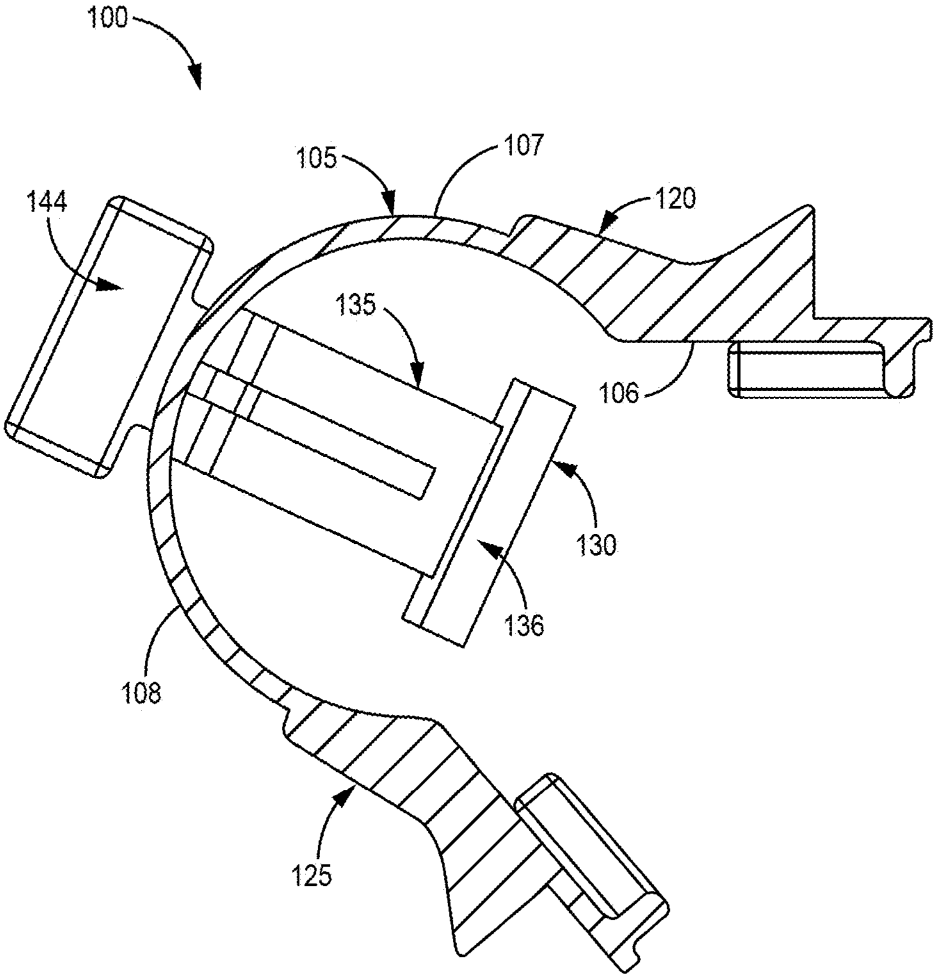
FIG. 6 is a radial cross-sectional view of the implant removal device of FIG. 1, taken along longitudinal line B-B in FIG. 5.

FIGS. 1-6 show an exemplary embodiment of an implant removal device 100 in isolation. Specifically, FIG. 1 illustrates a perspective view of the implant removal device 100, FIG. 2 illustrates a front end elevational view of the implant removal device 100, FIG. 3 illustrates a top plan view of the implant removal device 100, FIG. 4 illustrates a longitudinal cross-sectional view of the implant removal device 100 taken along longitudinal line A-A in FIG. 3, FIG. 5 illustrates a longitudinal side elevational view of the implant removal device 100, and FIG. 6 illustrates a radial cross-sectional view of the implant removal device 100 taken along longitudinal line B-B in FIG. 5.

The implant removal device 100 can be configured to be placed at a skin surface and facilitate removal of an implant that is located beneath the skin surface (a "subdermal implant"). For example, the implant removal device 100 can be configured to facilitate removal of an elongated rod implanted beneath the skin surface and having a longitudinal axis of the elongated rod extending generally parallel to the skin surface. Such an elongated rod implant beneath the surface of the skin could be, for instance, a contraceptive subdermal implant. In operation, the implant removal device 100 can be configured to impart one or more forces at the skin surface adjacent the subdermal implant and to help facilitate removal of the subdermal implant from the patient through an incision at the skin surface. For instance, in operation, the implant removal device 100 can be configured to impart one or more forces at the skin surface in a direction generally perpendicular to the longitudinal axis of the elongated rod (e.g., via one or more arms of the device 100) and/or impart one or more forces at the skin surface in a direction generally parallel to, and/or skewed relative to, the longitudinal axis of the elongated rod (e.g., via an extraction member of the device 100 in the skewed orientation when the extraction member is positioned generally downward at and onto the skin surface and in the parallel orientation when the extraction member is moved toward the incision).

As noted, FIGS. 1-6 show the implant removal device 100 in isolation. The illustrated embodiment of the implant removal device 100 is a single, integral piece device. As such, the device 100 may not have removable connections between the various components. In other embodiments within the scope of the present disclosure, the device 100 can be a multi-piece device with removable connections between two or more various components.

The implant removal device 100 can include a body 105. The body 105 includes a skin surface interfacing side 106 at least a portion of which can be configured to be positioned at a skin surface adjacent to, and underneath which skin surface is, an implant. For example, the body 105 can have a first lateral side 107 and a second lateral side 108, and the body 105 can be configured to be positioned such that at least a portion of the skin surface interfacing side 106 contacts the skin surface with the implant (located beneath the skin surface) between the first lateral side 107 and the second lateral side 108. In particular, when an incision is made at the skin surface (e.g., after the implant removal device 100 has been positioned and the arms moved to the skin gripping position), the body 105 can be configured to be positioned such that at least a portion of the skin surface interfacing side 106 contacts the skin surface near (e.g., adjacent to) an incision thereat such that the incision at the skin surface is located between the first lateral side 107 and the second lateral side 108.

The implant removal device 100 can include a first arm 120 and a second arm 125 each supported at the body 105. The first arm 120 can define a first arm longitudinal axis 123 along which a length of the first arm 120 extends, and the second arm 125 can define a second arm longitudinal axis 124 along which a length of the second arm 125 extends. Each of the first arm 120 and the second arm 125 is movable relative to the body 105 between a retracted position 122 and a skin gripping position 121 (e.g., with the arms 120, 125 being closer to one another and closer to extraction member 130 when in the skin gripping position 121). In the illustrated example, the first and second arms 120, 125 each pivot relative to the body 105, though in other embodiments the arms 120, 125 could move relative to the body 105 in other manners. As described further below, each of the first and second arm 120, 125 can be biased to the retracted position 122. FIGS. 1-6 show the first and second arms 120, 125 in one exemplary retracted position 122, and FIGS. 1 and 3 include a directional reference line to illustrate one exemplary skin gripping position 121 to which the first and second arms 120, 125 can be moved to from the retracted position 122. As this exemplary illustration shows, a space defined between the first arm 120 and the second arm 125 can be greater when the first and second arms 120, 125 are in the retracted position 122 than when the first and second arm 120, 125 are in the skin gripping position 121. When moved relative to the body 105 to the skin gripping position 121, the first and second arms 120, 125 are configured to contact and raise respective skin surfaces on opposite sides of the implant.

As best seen at FIGS. 1 and 2, the first arm 120 can include a first skin interfacing extension 118 and the second arm 125 can include a second skin interfacing extension 119. For example, the first skin interfacing extension 118 can extend out from the first arm 120 (e.g., extend out generally normal to an inner surface of the first arm 120) in a direction toward the second arm 125, and the second skin interfacing extension 119 can extend out from the second arm 125 (e.g., extend out generally normal to an inner surface of the second arm 125) in a direction toward the first arm 120. As such, it can be the case that the first and second arms 120, 125 are closest together at the locations of the first and second skin interfacing extensions 118, 119. The first skin interfacing extension 118 and the second skin interfacing extension 119 can be configured to serve as a contact point on the respective first and second arms 120, 125 with the skin surface at which the implant removal device 100 is positioned. And, as such, the first skin interfacing extension 118 and the second skin interfacing extension 119 can be configured to contact and raise up skin surface portions adjacent opposite longitudinal sides of the implant.

In some embodiments, such as that illustrated here, to help optimize the application of force at such skin surfaces via the first and second skin interfacing extensions 118, 119, one or both of the first and second skin interfacing extensions 118, 119 can include a contoured skin interfacing surface. For example, the first skin interfacing extension 118 can include a first skin interfacing surface 126 and the second skin interfacing extension 119 can include a second skin interfacing surface 127. The first skin interfacing surface 126 can be contoured to include a first skin interfacing surface first convex region 126A at an inner surface, generally facing the second arm 125, of the first skin interfacing extension 118, and the second skin interfacing surface 127 can be contoured to include a second skin interfacing surface first convex region 127A at an inner surface, generally facing the first arm 120, of the second skin interfacing extension 119. In one such embodiment, the first skin interfacing surface first convex region 126A can extend along a length (e.g., an entire length) of the inner surface of the first skin interfacing surface 126 and the second skin interfacing surface first convex region 127A can extend along a length (e.g., an entire length) of the inner surface of the second skin interfacing surface 127. In at least one such embodiment, the apex of the first skin interfacing surface first convex region 126A can define a closest portion of the first arm 120 to the second arm 125, and the apex of the second skin interfacing surface first convex region 127A can define a closest portion of the second arm 125 to the first arm 120.

Also in some embodiments, such as that illustrated here, the first skin interfacing extension 118 and the second skin interfacing extension 119 can be angled (e.g., skewed) relative to the respective inner surfaces of the first and second arms 120, 125 from which the first and second skin interfacing extensions 118, 119 extend out. For example, the first skin interfacing extension 118 can include a first skin interfacing extension proximal end 126B (e.g., closest to extraction member 130) and a first skin interfacing extension distal end 126C (e.g., furthest from extraction member 130) opposite the first skin interfacing extension proximal end 126B. And, the first skin interfacing extension 118 can be angled, relative to the first arm 120 inner surface from which the first skin interfacing extension 118 extends out, such that the first skin interfacing extension distal end 126C is at a higher elevation than the first skin interfacing extension proximal end 126B with the first skin interfacing extension 118 extending upward as the first skin interfacing extension 118 extends along a first skin interfacing extension central longitudinal axis 111 in a proximal to distal direction (e.g., extending in a direction away from extraction member 130). Also in this orientation, the first skin interfacing extension central longitudinal axis 111 can intersect the first arm longitudinal axis 123. Similarly, the second skin interfacing extension 119 can include a second skin interfacing extension proximal end 127B (e.g., closest to extraction member 130) and a second skin interfacing extension distal end 127C (e.g., furthest from extraction member 130) opposite the second skin interfacing extension proximal end 127B. And, the second skin interfacing extension 119 can be angled, relative to the second arm 125 inner surface from which the second skin interfacing extension 119 extends out, such that the second skin interfacing extension distal end 127C is at a higher elevation than the second skin interfacing extension proximal end 127B with the second skin interfacing extension 119 extending upward as the second skin interfacing extension 119 extends along a second skin interfacing extension central longitudinal axis 112 in a proximal to distal direction (e.g., extending in a direction away from extraction member 130). Also in this orientation, the second skin interfacing extension central longitudinal axis 112 can intersect the second arm longitudinal axis 124. Such angled orientation of the first and second skin interfacing extensions 118, 119 can be useful in inducing implant positioning, when the first and second arms 120, 125 are moved from the retracted position 122 to the skin gripping position 121, that helps to optimize precision of implant removal through an incision. Moreover, the extended out position of the first and second skin interfacing extensions 118, 119 can define one or more gaps adjacent the first and/or second skin interfacing extensions 118, 119 which can help to prevent other portions of the respective arms 120, 125 from unintentionally altering surface tension at the skin surface at which the device 100 is applied. The first and second skin interfacing extensions 118, 119 can define a length (e.g., defined in a direction of the axes 111, 112) ranging from 8 mm to 25 mm, from 10 mm to 22 mm, from 12 mm to 20 mm, or from 14 mm to 18 mm. The first and second skin interfacing extensions 118, 119 can define a height (e.g., defined in a direction generally perpendicular to the axes 111, 112 and extending perpendicular to the skin surface when the device 100 is positioned thereat) ranging from 0.5 mm to 4.0 mm, from 1.0 mm to 3.5 mm, or from 1.5 mm to 3.0 mm. It has been discovered that such configuration of the first and second skin interfacing extensions 118, 119 can be optimized for typical subdermal implant sizes in a way that alters surface tension at the skin surface where the first and second skin interfacing extensions 118, 119 are applied relative to normal, default surface tension at such skin surface and helps to localize stress applied by the first and second skin interfacing extensions 118, 119 at the skin surface at the location of the implant—the longitudinal sides of the implant—most helpful for stabilizing the implant for more efficient and improved patient comfort in implant removal.

As illustrated in this exemplary embodiment, the first skin interfacing surface 126 and the second skin interfacing surface 127 can face toward one another. The first skin interfacing surface 126 and the second skin interfacing surface 127 can each work together to apply one or more forces, at the skin surface adjacent the implant, to stabilize and position the implant for efficient removal. For example, when the arms 120, 125 are moved to the skin gripping position 121, the arms 120, 125 can contact and raise respective skin surfaces on opposite sides of the implant so as to thereby raise and position the implant between the first skin interfacing surface 126 and the second skin interfacing surface 127.

More specifically, as the arms 120, 125 are moved from the retracted position 122 toward the skin gripping position 121, each of the first skin interfacing surface first convex region 126A and the second skin interfacing surface first convex region 127A can allow excess skin at the skin surface to pass away from the interfacing first and second skin interfacing surfaces 126, 127 and, thereby, provide a more precise and stable positioning of the implant beneath this skin surface. In addition, the apex of each of the first skin interfacing surface first convex region 126A and the second skin interfacing surface first convex region 127A can apply a stabilizing force in a direction generally normal to the apex of each of the first skin interfacing surface first convex region 126A and the second skin interfacing surface first convex region 127A. Together, these stabilizing forces imparted on the skin surface via the apex of each of the first and second skin interfacing surface first convex regions 126A, 127A, as the arms 120, 125 are moved from the retracted position 122 toward the skin gripping position 121, can help to prevent the skin surface, and thus the implant underneath this skin surface, from moving downward back toward the adjacent skin surface.

Accordingly, the skin surface, and thus the implant underneath this skin surface, can be stabilized and its movement impeded in three directions—back (e.g., impeded from moving toward extraction member 130 and end of the device 100 opposite the arms 120, 125), down at one side (e.g., impeded from moving away from extraction member 130 and toward the skin surface interfacing side 106 at the first arm 120 side), and down at another (e.g., opposite) side (e.g., impeded from moving away from extraction member 130 and toward the skin surface interfacing side 106 at the second arm 125 side). As such, this configuration can resolve forces imparted at the skin surface, and thus at the implant underneath this skin surface, such that the implant has the forward directional degree of movement substantially unimpeded (e.g., substantially unimpeded to move in a direction of movement opposite to, and away from, extraction member 130). The resolution of these forces as such via the first and second skin interfacing surfaces 126, 127 and extraction member 130 can thus act to facilitate an efficient, precise, and repeatable process for stabilizing and removing the implant.

As referenced previously, the implant removal device 100 further includes extraction member 130 supported at the body 105. As illustrated, the extraction member 130 can be located between the first arm 120 and the second arm 125. In particular, the extraction member 130 can be located between the first arm 120 and the second arm 125 when the first and second arms 120, 125 are in the skin gripping position 121. The extraction member 130 can be configured to engage a skin surface at an end portion of the implant, which end portion extends between the first side of the implant and the second side of the implant, when the first and second arms 120, 125 are in the skin gripping position 121. Similarly, the extraction member 130 can be located between the first arm 120 and the second arm 125 when the first and second arms 120, 125 are in the retracted position 122.

In the illustrated embodiment of the implant removal device 100, the extraction member 130 can be fixed in place at the body 105. In this embodiment, the extraction member 130 can be configured to engage a skin surface at an end portion of the implant and the implant can be moved, using the extraction member 130, by moving the implant removal device 100, including the extraction member 130 fixed at the body 105, along, and relative to, the skin surface so as to cause the implant to move relative to the skin surface.

The extraction member 130 can be located at the body 105 such that the arms 120, 125 extend out from the body 105 beyond the extraction member 130. Also, the extraction member 130 can be located at the body 105 so as to extend to an elevation below the arms 120, 125. For instance, as illustrated, the extraction member 130 can extend below the first and second skin interfacing extensions 118, 119 (e.g., below the first skin interfacing extension proximal end 126B and the second skin interfacing extension proximal end 127B). Indeed, for the illustrated embodiment, the extraction member 130 can extend downward from its connection (e.g., integral connection) at the body 105 to be the lowest elevation component of the device 100. For instance, the extraction member bumper 136 can be spaced from 1 mm to 7 mm, from 2 mm to 6 mm, from 3 mm to 5 mm, or from 3.5 mm to 4.5 mm below the first and/or second skin interfacing extensions 118, 119, as measured from a center point of the extraction member bumper 136 to a lowest surface of one or both of the first and second skin interfacing extensions 118, 119. This position of the extraction member 130, relative to the arms 120, 125 and first and second skin interfacing extensions 118, 119 thereat, can help to facilitate extraction member 130 engagement at the skin surface (e.g., prior to first and second skin interfacing extensions 118, 119 engagement at the skin surface) adjacent the end portion of the implant which, as described further below, can help to move the implant, via the extraction member 130, relative to the skin surface and out through an incision at the skin surface.

The extraction member 130 can include an extraction member support flange 135 and an extraction member bumper 136. The extraction member support flange 135 can be connected (e.g., integral) to the body 105 and extend outward (e.g., and downward) from the body 105. In the illustrated embodiment, the extraction member support flange 135 extends downward away from the body 105 as it extends outward from the body 105. And, in this illustrated embodiment, the extraction member support flange 135 can include a reinforcing rib 137 to provide additional stability to the extraction member support flange 135 and thereby help to stabilize use of the extraction member 130 for removing the implant. The extraction member bumper 136 can be at a distal end of the extraction member support flange 135. As best seen at FIG. 2, for the illustrated embodiment, the extraction member bumper 136 is positioned at a lower elevation, and thus below, the first and second arms 120, 125 and positioned at a lower elevation, and thus below, the first and second skin interfacing extensions 118, 119.

The extraction member bumper 136 can be configured to engage the skin surface (e.g., prior to first and second skin interfacing extensions 118, 119 engagement at the skin surface) adjacent the end portion of the implant and apply force at this skin surface adjacent the end of the implant to help urge the implant out through an incision. In particular, the extraction member bumper 136 can transfer force (e.g., downward force in a direction toward the skin surface) applied at the body 105 to the skin surface adjacent the end portion of the implant. To help optimize the application of such force via the extraction member bumper 136, the extraction member bumper 136 can include a distal end 136A that includes a convexly curved surface. In some examples, the entirety of the distal end 136A can include the convexly curved surface. The extraction member bumper 136 can include the distal end 136A convexly curved surface, and, for embodiments where the extraction member bumper 136 has a generally circular cross-section, the extraction member bumper 136 can define a radius ranging from 0.5 mm to 10 mm, 0.5 mm to 5 mm, 0.5 mm to 4 mm, 1 mm to 4 mm, or 1 mm to 3 mm. The extraction member bumper 136 can have a width (e.g., defined in a direction extending along an axis that intersects the arms 120, 125) ranging from 15 mm to 35 mm, from 20 mm to 30 mm, or from 22 mm to 26 mm. And, the extraction member bumper 136 can have a height (e.g., defined in a direction extending along an axis that does not intersect the arms 120, 125 nor the extraction member support flange 135) ranging from 2 mm to 10 mm, from 4 mm to 8 mm, or from 5 mm to 7 mm. It has been discovered that such configuration of the extraction member bumper 136 can be optimized for typical subdermal implant sizes in a way that alters surface tension at the skin surface where the extraction member bumper 136 is applied relative to normal, default surface tension at such skin surface and helps to localize stress applied by the extraction member bumper 136 at the skin surface at the location of the implant—the end portion of the implant extending between the longitudinal sides of the implant—most helpful for urging the implant out through the incision and applying thereat sufficient force to help urge the implant out through an incision while minimizing patient discomfort.

The implant removal device 100 can additionally include an actuation interface 140 supported at the body 105. The actuation interface 140 can be configured to receive an actuation input thereat to cause at least one of the first arm 120 and the second arm 125 to move from the retracted position 122 to the skin gripping position 121. Namely, in the illustrated embodiment, the body 105 can be configured to impart a biasing force on each of the first arm 120 and the second arm 125 to bias each of the first and second arms 120, 125 to the retracted position 122. And, the body 105 can be configured such that this biasing force is overcome by application of the actuation input at the actuation interface 140 to cause each of the first and second arm 120, 125 to move from the retracted position 122 to the skin gripping position 121. Additionally, the body 105 can be configured such that, upon removal of the actuation input at the actuation interface 140, the biasing force acts to move each of the first and second arms 120, 125 from the skin gripping position 121 to the retracted position 122. This configuration can be useful in allowing a user to selectively modulate application of the actuation input at the actuation interface 140 to correspondingly control the extent to which the arms 120, 125 are moved from the retracted position 122 to the skin gripping position 121 which can allow the device 100 to be used across varying patient-to-patient anatomical characteristics at and around the skin surface and adjacent the implant.

In the illustrated example, the actuation interface 140 includes a first actuation interface 141 at the first arm 120 and a second actuation interface 142 at the second arm 125. For the illustrated embodiment, each of the first and second actuation interface 141, 141 defines a surface extension at the respective arm 120, 125 that is configured to receive a finger of a user (e.g., configured to receive one finger of a hand at the first actuation interface 141 and another finger of that same hand at the second actuation interface 142). The first actuation interface 141 can be configured to receive a first actuation input thereat to cause the first arm 120 to move from the retracted position 122 to the skin gripping position 121. In particular, the first actuation input can be applied at the first actuation interface 141 in a direction 143 to cause the first actuation interface 141 to move in the direction 143 and, as a result of applying the first actuation input at the first actuation interface 141 in the direction 143, move the first arm 120 from the retracted position 122 to the skin gripping position 121. And, likewise, the second actuation interface 142 can be configured to receive a second actuation input thereat to cause the second arm 125 to move from the retracted position 122 to the skin gripping position 121. In particular, the second actuation input can be applied at the second actuation interface 142 in a direction 144 149 to cause the second actuation interface 142 to move in the direction 144 149 and, as a result of applying the second actuation input at the second actuation interface 142 in the direction 144 149, move the second arm 125 from the retracted position 122 to the skin gripping position 121. Then, due to the bias force on the first and second arms 120, 125, when the first actuation input is removed from the first actuation interface 141 the first arm 120 can move from the skin gripping position 121 toward the retracted position 122, and when the second actuation input is removed from the second actuation interface 142 the second arm 125 can move from the skin gripping position 121 toward the retracted position 122.

As noted, the body 105 can be configured to impart a biasing force on each of the first arm 120 and the second arm 125 to bias each of the first and second arms 220, 225 to the retracted position 122. To help provide this biasing force, the body 105 can include a biasing member 145 that is configured to impart a biasing force on each of the first arm 120 and the second arm 125 to bias each of the first and second arm 120, 125 to the retracted position 122. In the illustrated embodiment, the first and second actuation interfaces 141, 142 are supported at the body 105 at the respective arm 120, 125 and spaced apart from the biasing member 145. In this way, the first and second actuation interfaces 141, 142 can act to transfer the force from the first and second actuation inputs applied, respectively, at the first and second actuation interfaces 141, 142 to the biasing member 145 and, as a result, overcome the biasing force imparted by the biasing member 145 and cause the arms 120, 125 to move toward the skin gripping position 121.

As one example, the biasing member 145 in the illustrated embodiment is in the form of a C-shaped element. The use of a C-shaped element as the biasing member 145 can help to distribute stresses and strains within the body 105 and, resultingly, allow the device 100 to be a smaller device while also providing appropriate structural stability. This C-shaped element can have a first C-shaped end 146 and a second C-shaped end 147 opposite the first C-shaped end 146. As shown, the first actuation interface 141 can be adjacent the first C-shaped end 146, and the second actuation interface 142 can be adjacent the second C-shaped end 147. The extraction member 130 can be supported at the body 105 at a general center of the C-shaped element generally midway between the C-shaped ends 146, 147. Notably, by locating the actuation interfaces 141, 142 adjacent the more linear C-shaped ends 146, 147, the amount of force needed from the actuation input to overcome the biasing force imparted by the biasing member 145 (e.g., C-shaped element) move the arms 120, 125 can be reduced and, thereby, increase user convenience associated with operation of the device 100.

The device 100, in some embodiments, can further include an extraction force applicator tab 144. The extraction force applicator tab 144 can be generally aligned at the body 105 with the location of the extraction member 130 such that the extraction force applicator tab 144 and the extraction member 130 both have a common axis (e.g., a common central longitudinal axis of the device 100, such as represented by line A-A in FIG. 3) running though each. The extraction force applicator tab 144 can be configured to receive an actuation input thereat, such as in a direction toward the extraction member 130, can when so applied the extraction force applicator tab 144 can transfer force from this actuation input to the extraction member 130 which in turn can transfer this force to the skin surface adjacent the end of the implant. For example, while a user has a portion (e.g., a first finger) of a hand at the first actuation interface 141 and another portion (e.g., a second finger) of that same hand at the second actuation interface 142, yet another portion of that same hand can be placed at the extraction force applicator tab 144 and used to apply the actuation input in the direction of the extraction member 130.

Figure 7:
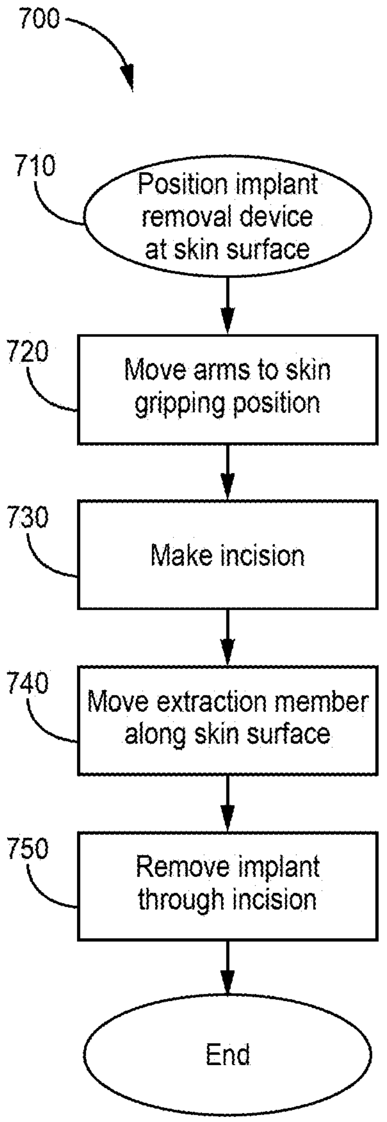
FIG. 7 is a flow diagram of an embodiment of a method of removing an implant (e.g., a subdermal implant).
Figure 8:
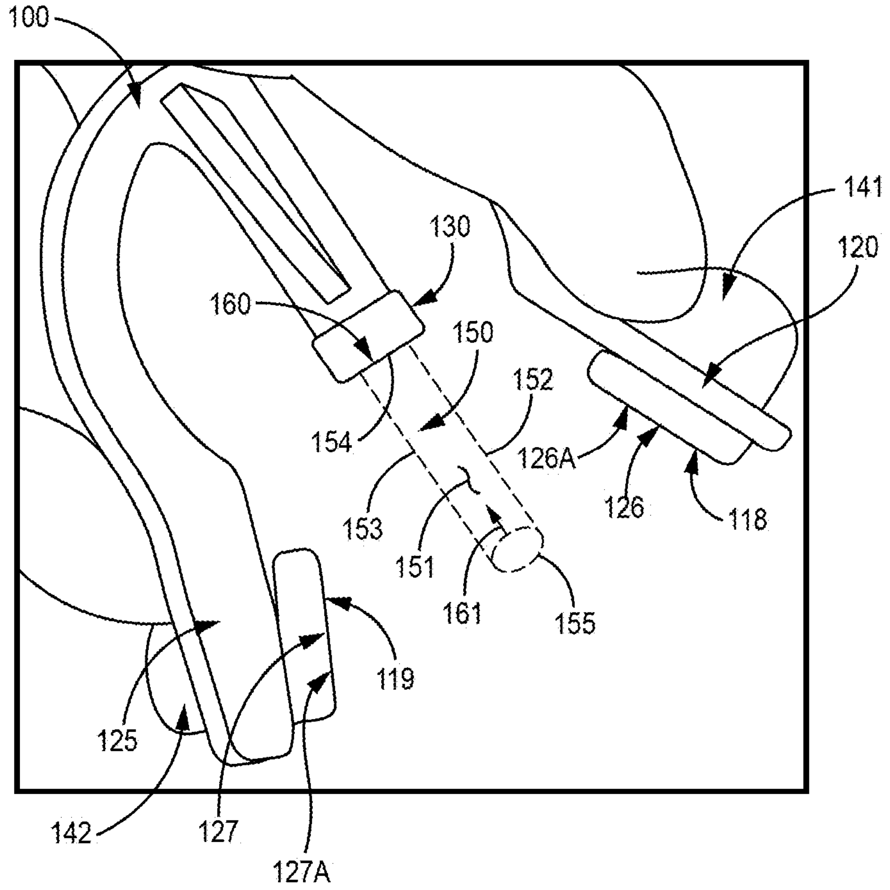
FIG. 8 is a perspective view of an implant removal device (e.g., the embodiment of the implant removal device of FIG. 1) with an extraction member of the implant removal device initially positioned in contact with a skin surface that is adjacent a first end of the implant with each of the first arm and the second arm in the retracted position.
Figure 9:
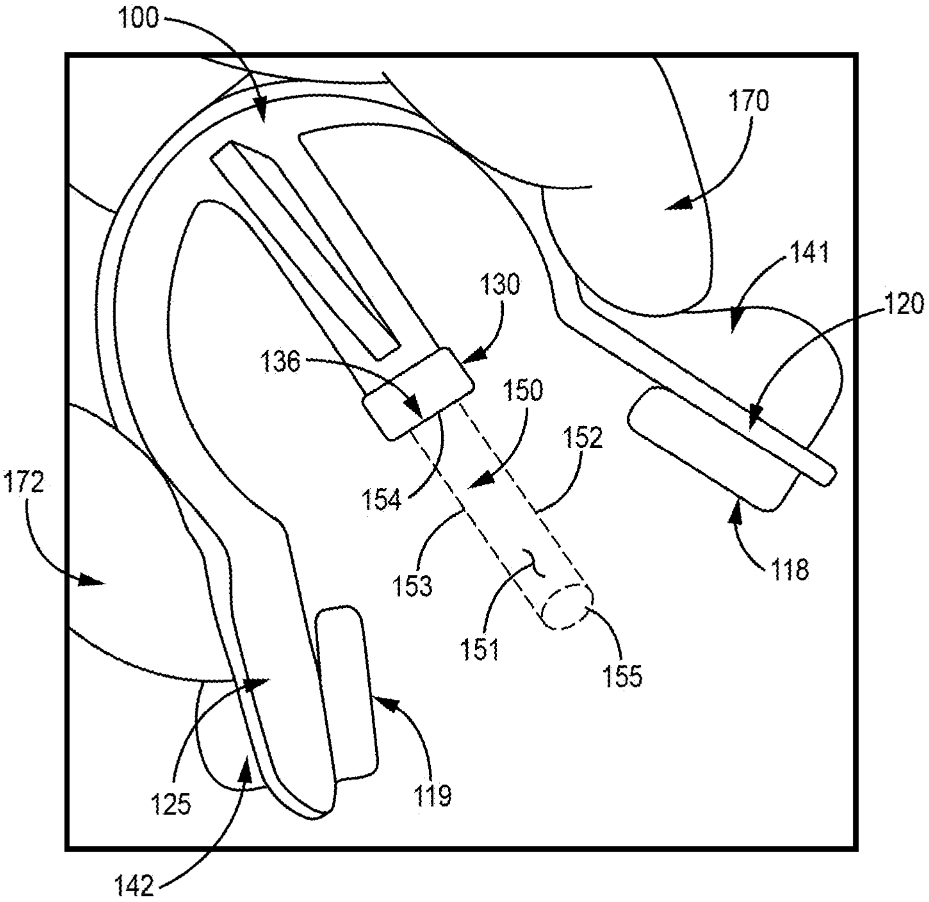
FIG. 9 is a perspective view of the implant removal device of FIG. 8 but now with the first arm and the second arm each positioned in contact with respective skin surfaces at respective opposite longitudinal sides of the implant yet still in the retracted position.
Figure 10:
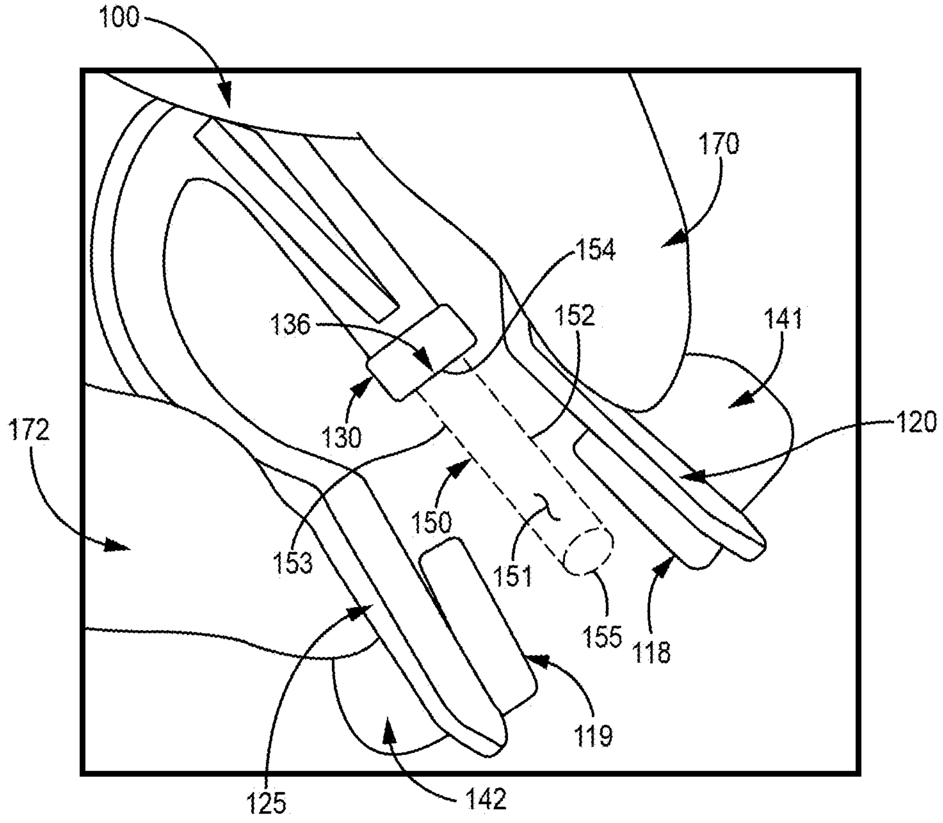
FIG. 10 is a perspective view of the implant removal device of FIG. 9 but now with the first arm and the second arm each moved from the retracted position to the skin gripping position.

As referenced above, in operation, the device 100 can be configured to facilitate removal of a subdermal implant. FIG. 7 is a flow diagram of an embodiment of a method 700 of removing an implant (e.g., a subdermal implant) using an implant removal device. One such embodiment of the method 700 can include use of the implant removal device 100 to remove the implant. As such, for exemplary purposes, FIGS. 8-10 show the implant removal device 100 being positioned and utilized at a skin surface having an implant (e.g., a subdermal implant) 150. Specifically, FIG. 8 is a perspective view of the implant removal device 100 with the extraction member 130 of the implant removal device 100 initially positioned in contact with a skin surface that is adjacent a first end of the implant with each of the first arm and the second arm in the retracted position. FIG. 9 is a perspective view of the implant removal device 100 but now with the first arm and the second arm each positioned in contact with respective skin surfaces at respective opposite longitudinal sides of the implant yet still in the retracted position. And, FIG. 10 is a perspective view of the implant removal device 100 but now with the first arm and the second arm each moved from the retracted position to the skin gripping position. To help illustrate certain portions of the method 700 shown at FIG. 7, the illustrations at FIGS. 8-10, showing positioning of the implant removal device 100, will be referenced as follows. Though other embodiments of the method 700 can be executed using a different implant removal device.

At step 710, the method 700 includes positioning the implant removal device 100 at a skin surface 151 that includes the implant 150 underneath the skin surface 151. The implant 150 has a first lateral implant side 152, a second lateral implant side 153 that is opposite the first side 152, and an implant end portion 154 that extends between the first side 152 and the second side 153. As shown at FIG. 8, the implant removal device 100 can be positioned at the skin surface 151 by initially positioning the extraction member 130 in contact with the skin surface 151 that is adjacent the implant end portion 154. Namely, given its relatively low elevation location at the implant removal device 100, the extraction member 130 can be the first component of the implant removal device 100 to contact the skin surface 151 and, as noted, the extraction member 130 can contact the skin surface 151 that is adjacent the implant end portion 154. The extraction member 130 can be moved downward toward the skin surface 151, in a direction 160, such that a generally downward force, in the direction 160, is imparted from the user's hand, to the extraction member 130, and to the implant end portion 154 that is adjacent the skin surface 151 at which the extraction member 130 is so initially positioned. Such generally downward applied force, in the direction 160, at the skin surface 151, which is adjacent the implant end portion 154, by the initially positioned extraction member 130 can cause a second, opposite end portion 155 of the implant 150 to move in a direction 161 (e.g., in an upward direction 161 opposite the downward direction 160 that force is applied by the extraction member 130) such that the second, opposite end portion 155 of the implant 150 can be caused to be angled generally upward, in the direction 161, toward the skin surface 151. The extraction member 130 can be so positioned at the skin surface 151 while the arms 120, 125 are in the retracted position and, after the extraction member 130 is so initially positioned, the arms 120, 125 can be brought to rest at the skin surface 151 while in the retracted position and with the implant 150 positioned between arms 120, 125 such that the first arm 120 is at a location spaced apart from a first lateral implant side 152 and the second arm 125 is at a location spaced apart from a second lateral implant side 153.

By so initially positioning the extraction member 130 to apply the generally downward force in the direction 160 at the skin surface 151 that is adjacent the implant end portion 154 and thereby causing the second, opposite end portion 155 of the implant 150 to move in the generally upward direction 161, a location of the second, opposite end portion 155 of the implant 150 underneath the skin surface 151 can become more readily ascertained by a user. For example, this can cause the second end portion 155 of the implant 150 to move closer to the skin surface 151 such that the second end portion 155 of the implant 150 is more readily visible underneath that skin surface 151. Indeed, in some application, this can cause the second end portion 155 of the implant 150 to "pop up" and "poke" at the skin surface 151 such that the location of the second end portion 155 of the implant 150 underneath the skin surface 151 is more readily visible via the more visible protrusion at this location of the skin surface 151. In particular, this movement of the second end portion 155 of the implant 150 in the direction 161 can cause the skin surface 151 to thin at the area of the second end portion 155 of the implant 150 (e.g., as a result of the initial placement of the extraction member inducing distension at the skin surface 151).

At step 720, once the implant removal device 100 is positioned at the skin surface 151, the method 700 includes moving at least one of the first arm 120 and the second arm 125 to the skin gripping position with the implant 150 between the first and second arms 120, 125. For example, step 720 can including moving each of the first arm 120 and the second arm 125 from the retracted position to the skin gripping position while the extraction member 130 is positioned in contact with the skin surface 151 adjacent the implant end portion 154 (e.g., and while the second, opposite implant end portion 155 is angled generally upward toward the skin surface 151 as a result of the extraction member 130 positioning and applied force). The first arm 120 can be moved from the retracted position to the skin gripping position so as to position the first arm 120 at the skin surface 151 adjacent the first lateral implant side 152, and the second arm 125 can be moved from the retracted position to the skin gripping position so as to position the second arm 125 at the skin surface 151 adjacent the second lateral implant side 153. Moving the first and/or second arm 120, 125 from the retracted position to the skin gripping position can cause the first and second arms 120, 125 to come closer together in the skin gripping position than in the retracted position. For example, when the first and second arms 120, 125 are in the retracted position, the first and second arms 120, 125 can be separated by an angle ranging from 100 degrees forty degrees, from eighty degrees to forty degrees, from seventy degrees to forty degrees, or from eighty degrees to fifty degrees. And, comparatively, when the first and second arms 120, 125 are in the skin gripping position, the first and second arms 120, 125 can be separated by an angle ranging from fifty degrees to five degrees, from forty degrees to five degrees, from thirty degrees to five degrees, from twenty degrees to five degrees, from fifteen degrees to five degrees, or from ten degrees to five degrees. The first and second arms 120, 125 can be moved from the retracted position to the skin gripping position at step 720 while the extraction member 130 is positioned at the skin surface 151 that is adjacent the implant end portion 154 to apply the generally downward force in the direction 160 at the skin surface 151 that is adjacent the implant end portion 154 (e.g., step 710).

The first and second arms 120, 125 can be moved from the retracted position to the skin gripping position as a result of an actuation input at the implant removal device 100. For instance, FIG. 9 shows the arms 120, 125 laid onto the skin surface 151 in the retracted position and with the extraction member 130 initially positioned in contact with the skin surface 151 that is adjacent the implant end portion 154, while FIG. 10 shows the arms 120, 125 moved from the retracted position of FIG. 9 to a skin gripping position at FIG. 10. In the illustrated embodiment, this can result from the user applying a first actuation input at the first arm 120 and a second actuation input at the second arm 125. For example, as shown here, the user can place one portion of a hand (e.g., a first finger 170) at the first actuation interface 141 and can pace another, different portion o that same hand (e.g., a second, different finger 171) at the second actuation interface 142. The user can then apply the first actuation input at the first arm 120 via the first actuation interface 141 at the first arm 120 and the second actuation input at the second arm 125 via the second actuation interface 142 at the second arm to cause the first and second arms 120, 125 to resultingly overcome the bias to the retracted position (e.g., bias force imparted on the arms 120, 125 via the body 105) and move to the skin gripping position.

As the one or more arms 120, 125 are moved from the retracted position (e.g., such as the retracted position shown at the example of FIG. 9) to the skin gripping position (e.g., such as the skin gripping position shown at the example of FIG. 10), the one or more arms 120, 125 can be configured to contact and raise the skin surface 151. In particular, as the first arm 120 is moved from the retracted position to the skin gripping position, the skin surface 151 interfacing with the first skin interfacing extension 118 and between the first skin interfacing extension 118 and the first lateral implant side 152 can be raised by movement of the first skin interfacing extension 118 along the such skin surface 151. Likewise, as the second arm 125 is moved from the retracted position to the skin gripping position, the skin surface 151 interfacing with the second skin interfacing extension 119 and between the second skin interfacing extension 119 and the second lateral implant side 153 can be raised by movement of the second skin interfacing extension 119 along the such skin surface 151. In some such instances, the configuration of the first and second skin interfacing extensions 118, 119 can result in the first and second skin interfacing extensions 118, 119 acting to scoop the implant 150 upward by inducing a change in surface tension at the skin surface 151 adjacent the implant 150. In this way, moving the arms 120, 125 from the retracted position to the skin gripping position can cause the first and second skin interfacing extensions 118, 119 to raise upward the skin surfaces 151 that are adjacent opposite longitudinal sides 152, 153 of the implant 150 and, thereby, raise upward the implant 150 that is underneath the raised by skin surface 151.

The combination of the extraction member 130 positioned at the skin surface 151 that is adjacent the implant end portion 154 to apply the generally downward force in the direction 160 at the skin surface 151 that is adjacent the implant end portion 154 (e.g., step 710) and the movement of the arms 120, 125 from the retracted position to the skin gripping position (e.g., step 720) can result in altering the orientation of the implant 150 underneath the skin surface 151 in a way that is favorable to more precise, efficient, and comfortable implant 150 removal. Namely, as noted, positioning the extraction member 130 at the skin surface 151 that is adjacent the implant end portion 154 to apply the generally downward force in the direction 160 at the skin surface 151 that is adjacent the implant end portion 154 can cause the second, opposite end portion 155 of the implant 150 to move in the generally upward direction 161 and can thereby render the location of the second, opposite end portion 155 of the implant 150 underneath the skin surface 151 more readily ascertained by a user. This can help to increase the locational precision (e.g., and thus help to reduce the size (e.g., length, width, and/or depth) of) of a subsequently made incision at the skin surface 151. And, as noted, moving the arms 120, 125 from the retracted position to the skin gripping position can cause the first and second skin interfacing extensions 118, 119 to raise upward the skin surfaces 151 that are adjacent opposite longitudinal sides 152, 153 of the implant 150 and can thereby act to help hold the implant 150 is such position, and thereby help stabilize the position of the implant 150 underneath the skin surface 151, as a result of the change in surface tension at the skin surface 151 caused by the movement of the first and second skin interfacing extensions 118, 119 along the skin surface 151 and to the skin gripping position. This increased stability of the implant 150 can help to increase the ease and efficiency of, and reduce patient discomfort associated with, removing the implant 150 through a subsequently made incision at the skin surface 151. For example, because moving the arms 120, 125 from the retracted position to the skin gripping position can cause the first and second skin interfacing extensions 118, 119 to raise upward the skin surfaces 151 that are adjacent opposite longitudinal sides 152, 153 of the implant 150, the implant 150 can be caused to be positioned closer to the skin surface and thereby necessitate a shallower depth of incision than would otherwise be needed for conventional removal of the implant 150.

At step 730, the method 700 can optionally include making an incision at the skin surface 151. The incision can be made at the skin surface, at step 730, after the implant removal device is positioned at step 710 and after the at least one arm 120, 125 has been moved to the skin gripping position at step 720. As such, the incision can be made at step 720 while the implant 150 is oriented with the second end portion 155 of the implant 150 angled upward and the skin surfaces 151 that are adjacent opposite longitudinal sides 152, 153 of the implant 150 are raised upward. The incision can be made at the skin surface 151 that is adjacent the second end portion 155 of the implant 150. As noted previously, making the incision at the skin surface 151 that is adjacent the second end portion 155 of the implant 150 while the implant 150 is oriented with the second end portion 155 of the implant 150 angled upward and the skin surfaces 151 that are adjacent opposite longitudinal sides 152, 153 of the implant 150 are raised upward can allow for a smaller, more precise incision since the location of the second end portion 155 of the implant 150 can be better ascertained and can allow for improved removal efficient and patient comfort as the stability of the implant 150 underneath the skin surface 151 is improved.

At step 740, the method 700 can optionally include moving the extraction member 130 of the implant removal device 100 along the skin surface 151. For instance, moving the extraction member 130 along the skin surface 151 can include a user applying an actuation input (e.g., actuation force) on the extraction member 130 (e.g., via the extraction force applicator tab 144) at least in a direction toward the incision. For example, this can include a user applying the actuation input in both a downward direction toward the skin surface 151 at a location adjacent the adjacent the implant end portion 154 and a direction toward the incision. Step 740 can occur after the incision is made at step 730, and, thus, moving the extraction member 130 along the skin surface 151 can include moving the extraction member 130 along the skin surface 151 toward the incision. For embodiments where the extraction member 130 is integral to the body of the implant removal device, moving the extraction member 130 along the skin surface 151 can include moving the extraction member 130 with the body of the implant removal device. With the extraction member 130 positioned at the skin surface 151 that is adjacent the implant end portion 154 of the implant 150 and the incision made at the skin surface 151 that is adjacent the second end portion 155 of the implant 150, moving the extraction member 130 at step 740 when so positioned can cause the extraction member 130 to help urge the implant 150 out through the incision. Moving the extraction member 130 at step 740 can include moving the extraction member 130 relative to the skin surface 151 and thus moving the implant 150, using the extraction member 130, relative to, and underneath, the skin surface 151.

At step 750, the method 700 can optionally include removing the implant 150 through the incision. As the second end portion 155 of the implant 150 is moved toward the incision (e.g., as a result of moving the extraction member 130 at step 740), the second end portion 155 of the implant 150 can begin to exit from underneath the skin surface 151 through the incision. When this occurs, a user can grasp (e.g., using a surgical forceps device) the second end portion 155, which has emerged out from underneath the skin surface 151 through the incision, to further help remove the implant 150.

As will be appreciated from the details of the present disclosure, the implant removal subject matter disclosed herein can provide a number of useful advantages. Notably, various features of the implant removal described herein can be configured in operation, as described, to leverage the natural surface tension present at the skin surface 151. For example, the previously described configuration of the first and second skin interfacing extensions 118, 119 at the respective arms 120, 125 can be useful in operation in scooping, retaining, and supporting the implant 150 at an elevated location between the arms 120, 125 while at the same time allowing for the natural surface tension present at the skin surface 151 to draw excess skin at the skin surface 151 around (e.g., through a gap present between the respective first and second skin interfacing extensions 118, 119 and the respective arm 120, 125), and out through and under, the arms 120, 125 so as to provide a more stabilized retention of the implant 150 between the arms 120, 125.

Also notable, various features of the implant removal described herein can allow for the incision to be made in a more efficient and precise manner. Namely, various features of the implant removal device described herein can work in operation such that the implant removal device can be used to reorient and retain the implant between the arms 120, 125 before creating the incision at the skin surface. By allowing for the incision to be made once the location of the implant has been ascertained and the implant has stabilized in its reoriented position between the arms 120, 125, the size of the incision can be minimized and, as a result, patient discomfort, wound closure effort and resources, and recovery time associated with the implant removal procedure can each be meaningfully reduced.

Figure 11:
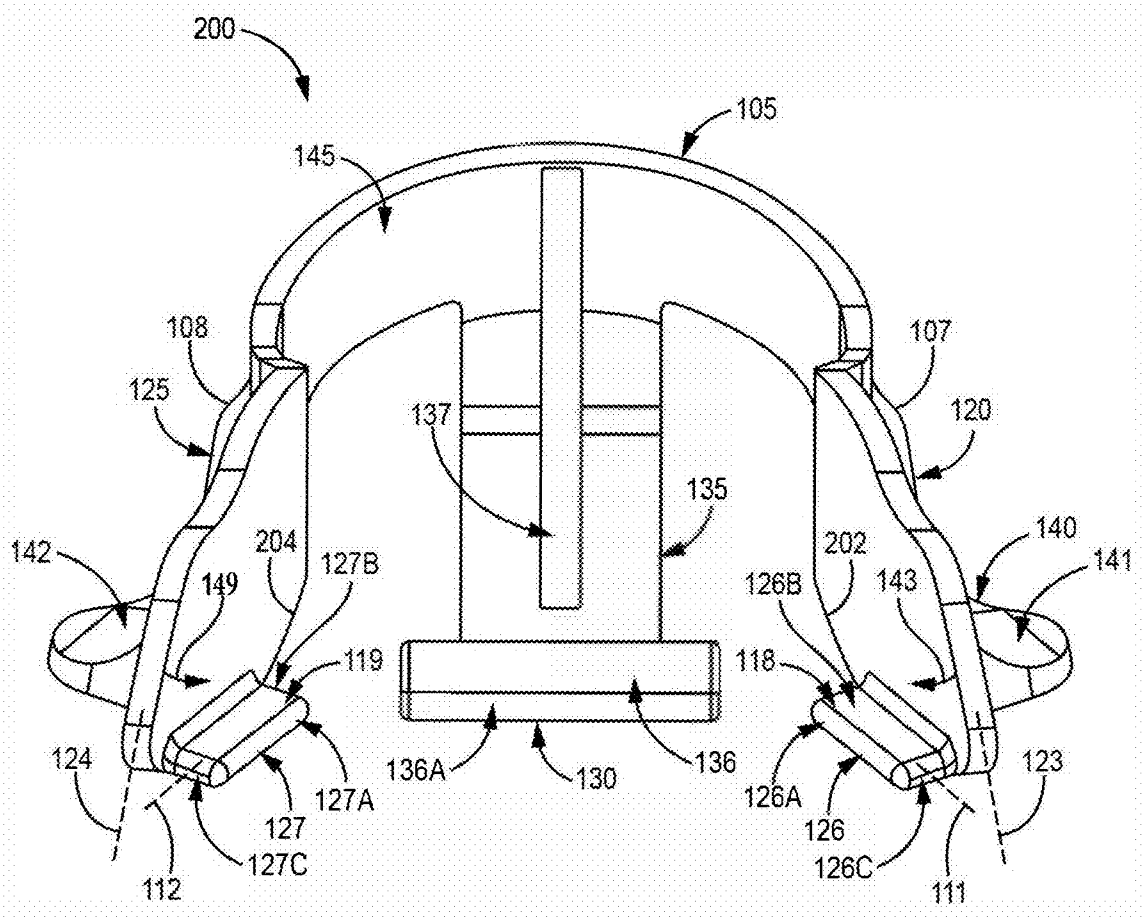
FIG. 11 is a front end elevational view of another embodiment of an implant removal device.

FIG. 11 illustrates a front end elevational view of another embodiment of an implant removal device 200. The implant removal device 200 can be similar to, or the same as, the implant removal device 100 described and illustrated previously except as otherwise noted here.

The body 105 of the implant removal device 200 can include a first bottom skin interfacing surface portion 202 at the skin surface interfacing side 106 of the first arm 120 and a second bottom skin interfacing surface portion 204 at the skin surface interfacing side 106 of the second arm 125. The first bottom skin interfacing surface portion 202 can be located proximal of the first skin interfacing extension 118, for instance, such that the first bottom skin interfacing surface portion 202 extends proximally from the first skin interfacing extension 118 a distance toward the biasing member 145. Likewise, the second bottom skin interfacing surface portion 204 can be located proximal of the second skin interfacing extension 119, for instance, such that the second bottom skin interfacing surface portion 204 extends proximally from the second skin interfacing extension 119 a distance toward the biasing member 145. As with the implant removal device 100, the implant removal device 200 can include the first and second arms 120, 125 symmetrical about the extraction member support flange 135 and, thus, the first and second bottom skin interfacing surface portions 202, 204 can extend a same distance proximally from the respective first and second skin interfacing extensions 118, 119.

As shown for the illustrated embodiment of the implant removal device 200, each of the first bottom skin interfacing surface portion 202 and the second bottom skin interfacing surface portion 204 can be generally linear or concave as it extends from the respective first and second skin interfacing extensions 118, 119. For example, as illustrated, each of the first bottom skin interfacing surface portion 202 and the second bottom skin interfacing surface portion 204 form a relatively small degree of concavity at the skin surface interfacing side 106 of the respective first and second arms 120, 125 (though in other examples the implant removal device 200 can include the first and second bottom skin interfacing surface portions 202, 204 as linear as each extends from the respective first and second skin interfacing extensions 118, 119). Whereas for the implant removal device 100 the same location at the skin surface interfacing side 106 can include a convex curvature extending inward along the skin surface interfacing side 106 at the first and second arms 120, 125. In certain instances, for example, the presence of the linear or convex geometry at the first and second bottom skin interfacing surface portions 202, 204 of the implant removal device 200 can be useful in applying added contact force at the skin surface at which the implant removal device 200 is placed so as to resultingly help provide additional stabilization force along opposite side portions of the subdermal implant.

Various non-limiting exemplary embodiments have been described. It will be appreciated that suitable alternatives are possible without departing from the scope of the examples described herein.

What is claimed is:

1. An implant removal device comprising:
- a body comprising a biasing member;
- a first arm supported at the body, the first arm configured to move relative to the body between a first arm retracted position and a first arm skin gripping position;
- a second arm supported at the body, the second arm configured to move relative to the body between a second arm retracted position and a second arm skin gripping position;
- a first actuation interface supported at the body and configured to receive an actuation input to cause the first arm to move between the first arm retracted position and the first arm skin gripping position;
- a second actuation interface supported at the body and configured to receive an actuation input to cause the second arm to move between the second arm retracted position and the second arm skin gripping position; and
- an extraction member fixed in place at the body, the extraction member comprising a proximal extraction member end supported at the body and a distal extraction member end located between the first arm and the second arm, wherein the first arm and the second arm each define an arm length that extends beyond the distal extraction member end, and wherein the extraction member is configured to remain stationary relative to the body while the first arm and the second arm are moved relative to the body, and wherein the extraction member comprises a support flange and a reinforcing rib directly connected to the body, the support flange extending out from the body and the reinforcing rib configured to provide a stabilizing force at the support flange when the extraction member contacts a skin surface,
- wherein the first actuation interface comprises a first flange that extends out from the first arm in a direction away from the extraction member, and wherein the second actuation interface comprises a second flange that extends out from the second arm in a direction away from the extraction member, wherein the extraction member comprises a support flange and a reinforcing rib, the support flange extending out from the body and the reinforcing rib configured to provide a stabilizing force at the support flange when the extraction member contacts a skin surface, and wherein the reinforcing rib is directly connected to the body,
- wherein the biasing member is configured to impart a biasing force at each of the first arm and the second arm to bias the first arm to the first arm retracted position and the second arm to the second arm retracted position, wherein the biasing member comprises a C-shaped element having a curved body, a first element end at one end of the curved body, and a second element end at another opposite end of the curved body, and wherein the first flange extends out from the first arm at the first element end and the second flange extends out from the second arm at the second element end, and
- wherein the implant removal device is a single, integral piece.

2. The device of claim 1, wherein the first arm is configured to be maintained at the first arm skin gripping position while a first actuation input is maintained at the first actuation interface and the first arm is configured to move, as a result of the bias, from the first arm skin gripping position to the first arm retracted position when the first actuation input is removed from the first actuation interface, and wherein the second arm is configured to be maintained at the second arm skin gripping position while a second actuation input is maintained at the second actuation interface and the second arm is configured to move, as a result of the bias, from the second arm skin gripping position to the second arm retracted position when the second actuation input is removed from the second actuation interface.

3. The device of claim 2, wherein the first flange is configured to receive the first actuation input via at least a first finger of a first hand at the first flange, and wherein the second flange is configured to receive the second actuation input via at least a second finger of the first hand at the second flange.

4. The device of claim 1, further comprising:
- a first skin interfacing extension at a side of the first arm opposite the first actuation interface, the first skin interfacing extension extending out from the first arm toward the second arm; and
- a second skin interfacing extension at a side of the second arm opposite the second actuation interface, the second skin interfacing extension extending out from the second arm toward the first arm.

5. The device of claim 4, wherein the first skin interfacing extension is configured to serve as a contact point, at the first arm, with a skin surface at which the implant removal device is positioned so as to contact and raise up the skin surface adjacent the first arm, and wherein the second skin interfacing extension is configured to serve as a contact point, at the second arm, with the skin surface at which the implant removal device is positioned so as to contact and raise up the skin surface adjacent the second arm.

6. The device of claim 1, wherein, when the implant removal device is positioned at a skin surface, the extraction member is configured to contact the skin surface adjacent a first end of an implant that extends between a first longitudinal side of the implant and a second longitudinal side of the implant, wherein, when the implant removal device is positioned at the skin surface and the first arm is at the first arm skin gripping position, the first arm is configured to contact the skin surface adjacent the first longitudinal side of the implant, and wherein, when the implant removal device is positioned at the skin surface and the second arm is at the second arm skin gripping position, the second arm is configured to contact the skin surface adjacent the second longitudinal side of the implant.

7. The device of claim 6, wherein the first arm is configured, when moved from the first arm retracted position to the first arm skin gripping position, to contact and raise upward the skin surface adjacent the first longitudinal side of the implant, and wherein the second arm is configured, when moved from the second arm retracted position to the second arm skin gripping position, to contact and raise upward the skin surface adjacent the second longitudinal side of the implant.

8. The device of claim 7, wherein, as the extraction member is moved toward an incision at the skin surface and with the first arm in the first arm skin gripping position and the second arm in the second arm skin gripping position, the extraction member is configured to urge the implant toward the incision.

9. The device of claim 6, wherein the extraction member is positioned below the first arm and the second arm and the extraction member defines a bottom-most surface of the implant removal device, wherein the extraction member defines a length, measured from the proximal extraction member end to the distal extraction member end, that is shorter than a length of the first arm and the second arm.

10. The device of claim 9, wherein a top-most surface of the implant removal device, which is opposite the bottom-most surface, defines between the first arm and the second arm an opening over the extraction member.

11. An implant removal device comprising:

a body comprising a biasing member;

a first arm supported at the body, the first arm configured to move relative to the body between a first arm retracted position and a first arm skin gripping position;

a second arm supported at the body, the second arm configured to move relative to the body between a second arm retracted position and a second arm skin gripping position;

a first actuation interface supported at the body and configured to receive an actuation input to cause the first arm to move between the first arm retracted position and the first arm skin gripping position;

a second actuation interface supported at the body and configured to receive an actuation input to cause the second arm to move between the second arm retracted position and the second arm skin gripping position; and an extraction member supported fixed in place at the body and located between the first arm and the second arm, wherein the extraction member is positioned below the first arm and the second arm and the extraction member defines a bottom-most surface of the implant removal device, and wherein the extraction member defines a length that is shorter than a length of the first arm and the second arm, and wherein the extraction member is configured to remain stationary relative to the body while the first arm and the second arm are moved relative to the body, and wherein the extraction member comprises a support flange and a reinforcing rib directly connected to the body, the support flange extending out from the body and the reinforcing rib configured to provide a stabilizing force at the support flange when the extraction member contacts a skin surface, wherein the first actuation interface comprises a first flange that extends out from the first arm in a direction away from the extraction member, and wherein the second actuation interface comprises a second flange that extends out from the second arm in a direction away from the extraction member, wherein the biasing member is configured to impart a biasing force at each of the first arm and the second arm to bias the first arm to the first arm retracted position and the second arm to the second arm retracted position, wherein the biasing member comprises a C-shaped element having a curved body, a first element end at one end of the curved body, and a second element end at another opposite end of the curved body, and wherein the first flange extends out from the first arm at the first element end and the second flange extends out from the second arm at the second element end.

12. An implant removal device comprising:

a body comprising a biasing member;

a first arm supported at the body, the first arm configured to move relative to the body between a first arm retracted position and a first arm skin gripping position;

a second arm supported at the body, the second arm configured to move relative to the body between a second arm retracted position and a second arm skin gripping position;

a first actuation interface supported at the body and configured to receive an actuation input to cause the first arm to move between the first arm retracted position and the first arm skin gripping position;

a second actuation interface supported at the body and configured to receive an actuation input to cause the second arm to move between the second arm retracted position and the second arm skin gripping position; and an extraction member supported fixed in place at the body and having a length shorter than that of the first arm and the second arm, wherein when the implant removal device is positioned at a skin surface, the extraction member is configured to contact the skin surface between the first arm and the second arm and adjacent a first end of an implant that extends between a first longitudinal side of the implant and a second longitudinal side of the implant, wherein the extraction member is configured to remain stationary relative to the body while the first arm and the second arm are moved relative to the body, and wherein the extraction member comprises a support flange and a reinforcing rib directly connected to the body, the support flange extending out from the body and the reinforcing rib configured to provide a stabilizing force at the support flange when the extraction member contacts a skin surface, wherein the first actuation interface comprises a first flange that extends out from the first arm in a direction away from the extraction member, and wherein the second actuation interface comprises a second flange that extends out from the second arm in a direction away from the extraction member, wherein the biasing member is configured to impart a biasing force at each of the first arm and the second arm to bias the first arm to the first arm retracted position and the second arm to the second arm retracted position, wherein the biasing member comprises a C-shaped element having a curved body, a first element end at one end of the curved body, and a second element end at another opposite end of the curved body, and wherein the first flange extends out from the first arm at the first element end and the second flange extends out from the second arm at the second element end.

13. The device of claim 12, wherein the first flange is configured to receive a first actuation input via at least a first finger of a first hand at the first flange to cause the first arm to move from the first arm retracted position to the first arm skin gripping position, and the second flange is configured to receive a second actuation input via at least a second finger of the first hand at the second flange to cause the second arm to move from the second arm retracted position to the second arm skin gripping position.

14. The device of claim 12, wherein the first arm is configured to be maintained at the first arm skin gripping position while a first actuation input is maintained at the first actuation interface and the first arm is configured to move, as a result of the bias, from the first arm skin gripping position to the first arm retracted position when the first actuation input is removed from the first actuation interface, and wherein the second arm is configured to be maintained at the second arm skin gripping position while a second actuation input is maintained at the second actuation interface and the second arm is configured to move, as a result of the bias, from the second arm skin gripping position to the second arm retracted position when the second actuation input is removed from the second actuation interface.

* * * * *